(12) United States Patent
Kramer

(10) Patent No.: US 6,599,858 B1
(45) Date of Patent: *Jul. 29, 2003

(54) PROCESS FOR MAKING AMMONIUM GLYPHOSATE FLAKES

(75) Inventor: Richard M. Kramer, Chesterfield, MO (US)

(73) Assignee: Monsanto Technology LLC, St. Louis, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 09/703,077

(22) Filed: Jul. 25, 2000

Related U.S. Application Data
(60) Provisional application No. 60/146,261, filed on Jul. 29, 1999.

(51) Int. Cl.$^7$ .......................... A01N 57/18; C07F 9/22; C07F 9/28
(52) U.S. Cl. ......................................... 504/206; 562/17
(58) Field of Search ............................. 562/17; 504/206

(56) References Cited

U.S. PATENT DOCUMENTS

| | | | |
|---|---|---|---|
| 4,405,531 A | * 9/1983 | Franz | 260/501.12 |
| 5,047,079 A | 9/1991 | Djafar et al. | 71/86 |
| 5,070,197 A | 12/1991 | Chin et al. | 544/11 |
| 5,266,553 A | 11/1993 | Champion | 504/206 |
| 5,324,708 A | 6/1994 | Moreno | 504/206 |
| 5,410,075 A | 4/1995 | Moreno et al. | 562/17 |
| 5,612,285 A | 3/1997 | Arnold | 504/206 |
| 5,614,468 A | 3/1997 | Kramer et al. | 504/206 |
| 5,633,397 A | 5/1997 | Gillespie et al. | 562/17 |
| 5,693,593 A | 12/1997 | Arnold | 504/206 |
| 5,716,903 A | 2/1998 | Kramer et al. | 504/206 |
| 6,448,434 B1 | * 9/2002 | Kramer | 562/17 |

FOREIGN PATENT DOCUMENTS

| | | | |
|---|---|---|---|
| EP | 0 378 985 | 7/1990 | A01N/57/20 |
| EP | 0 582 561 | 2/1994 | A01N/57/20 |
| WO | WO87/04595 | 8/1987 | A01N/57/20 |
| WO | WO90/07275 | 7/1990 | A01N/57/20 |
| WO | WO94/10844 | 5/1994 | A01N/57/20 |
| WO | WO96/40696 | 12/1996 | C07F/9/38 |
| WO | WO92/12637 | 8/1999 | A01N/57/20 |

OTHER PUBLICATIONS

Takahashi, G. "Studies on the Pesticide Formulation and Jet Mill" Funtai to Kogyo, vol. 19(10), pp. 35–40 (1987). As abstracted by CAPLUS.*

Kirk–Othmer Encyclopedia of Chemical Technology: "Size Reduction" John Wiley & Sons, Inc. (1997).*

The Merck Index 13$^{th}$ Ed. Merck & Co., Inc. Whitehouse Station, NJ, USA, p. 87 (2001).*

"Alfa Aesar Research Chemicals, Metals and Materials 1999–2000" Catalog, p. 50. (1999).*

* cited by examiner

Primary Examiner—Richard L. Raymond
Assistant Examiner—Zachary C. Tucker
(74) Attorney, Agent, or Firm—Senniger, Powers, Leavitt & Roedel; Joseph A. Schaper

(57) ABSTRACT

A process is provided for preparing ammonium glyphosate flakes, comprising (a) mixing (i) solid particulate glyphosate acid, (ii) water in an amount of about 0.5 to about 3 parts by weight per part by weight of glyphosate acid, and (iii) a base that supplies ammonium cations, in an amount of about 0.8 to about 1.25 mole equivalents of ammonia per mole of glyphosate acid, to form an aqueous reaction medium; (b) allowing the glyphosate acid to react with the base in the reaction medium to form a reaction product comprising a concentrated aqueous solution of ammonium glyphosate; (c) drying the reaction product by contact thereof with a heated surface to form, primarily by evaporation of water, a solid deposit on the heated surface; and (d) scraping the solid deposit off the heated surface to recover dry flakes of ammonium glyphosate.

5 Claims, 1 Drawing Sheet

PROCESS FOR MAKING AMMONIUM GLYPHOSATE FLAKES

This application claims the benefit of U.S. Provisional Application No. 60/146,261, filed Jul. 29, 1999.

FIELD OF THE INVENTION

The present invention relates to preparation of a herbicidal composition useful in agriculture and in other situations where control of weeds or other vegetation is desired. In particular, it relates to preparation of a herbicidal active ingredient, namely N-phosphonomethylglycine (glyphosate) in the form of the ammonium salt thereof, as a finished product or as an intermediate useful in further processing.

BACKGROUND OF THE INVENTION

Glyphosate herbicides, especially herbicides comprising a water-soluble salt of glyphosate, are well known. Specifically, the monoammonium salt of glyphosate is disclosed as a useful herbicide for example in U.S. Pat. No. 4,405,531 to Franz. Unless the context demands otherwise, "ammonium glyphosate" herein refers to the monoammonium salt of glyphosate, which has the chemical formula

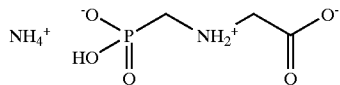

it being understood that the mole ratio of ammonium cations to glyphosate anions in such a salt is not necessarily exactly 1. A slight molar excess of either ammonium cations or glyphosate anions, for example providing a mole ratio of about 0.8 to about 1.25, is not inconsistent with the term "ammonium glyphosate" as used herein.

Ammonium glyphosate is the primary salt of choice in the preparation of dry glyphosate herbicide formulations. A "dry" formulation herein is a composition that is solid, usually particulate, wherein particles are either aggregated as in a granular composition or non-aggregated as in a powder. The word "dry" in this context does not imply that the formulation is necessarily free of water or other liquid, only that it is dry to the touch. Dry formulations can contain up to about 5% by weight of water, but more typically the water content is less than about 1%, for example about 0.5% or lower.

Dry formulations of glyphosate herbicides, like the corresponding liquid (normally aqueous) formulations, typically contain one or more surfactants in addition to the glyphosate salt. Surfactants are important components of glyphosate formulations because, when a glyphosate formulation is diluted, dissolved or dispersed in water for application by spraying to foliage of plants, the surfactants assist in retention of droplets of the spray by the foliage, adhesion of the spray droplets to the foliar surface and penetration of the glyphosate through the hydrophobic cuticle that covers the foliar surface, by these means and possibly in other ways enhancing herbicidal effectiveness of the glyphosate spray.

However, a surfactant is not an essential component of a glyphosate formulation. The end-user can add a non-surfactant-containing glyphosate formulation to a spray tank together with a surfactant, a procedure known as tank-mixing. In some cases, a glyphosate herbicide can be successfully applied without any surfactant. This is particularly true where the dose rate of the glyphosate is rather high, for example above about 1 kg acid equivalent (a.e.)/ha.

Ammonium glyphosate is the preferred salt for use in preparing dry glyphosate formulations for a number of reasons, but perhaps mainly for the reason that ammonium glyphosate is relatively non-hygroscopic. Salts favored for preparation of aqueous formulations, such as the isopropylammonium salt or the trimethylsulfonium salt, are very difficult to dry down to a crystalline state and, once dry, have a strong tendency to reabsorb water. Dry glyphosate formulations based on the ammonium salt are disclosed for example in U.S. Pat. No. 5,656,572 to Kuchikata et al.

The sodium salt, disclosed to be useful in dry glyphosate herbicide formulations for example in International Patent Application No. WO 87/04595, is much less hygroscopic than these salts but nonetheless requires packaging with a very water-impermeable material to avoid absorption of water vapor from the atmosphere and consequent loss of free-flowing properties. U.S. Pat. No. 5,324,708 to Moreno et al. discloses a process for preparing a non-hygroscopic monoammonium glyphosate; however, dry ammonium glyphosate prepared by any known process is adequately non-hygroscopic for most practical purposes.

U.S. Pat. No. 5,266,553 to Champion & Harwell discloses a process for preparing a dry water-soluble composition comprising a salt of a herbicidal compound that includes a carboxylic acid functionality. This process comprises forming an aqueous solution or slurry of such a salt by reacting the herbicidal compound with a neutralizing base in the presence of water, and thereafter removing the water to provide the dry salt. The process is directed particularly at substituted benzoic acid herbicides and phenoxy-substituted carboxylic acid herbicides, but is said to be useful also for glyphosate. The drying method is specified to be one that is controlled such that the temperature of the herbicidal salt does not exceed 80° C.; drying under vacuum is preferred, and use of a continuous thin-film dryer or a scraped surface heat exchanger is said to be unsuitable because of the prolonged drying period necessary or because an amorphous paste is produced.

Solid-state reaction of glyphosate acid and ammonium bicarbonate, as disclosed for example in above-referenced U.S. Pat. No. 5,656,572, produces a particulate ammonium glyposate that can be used directly as a herbicidal product, or granulated, for example by pan granulation, to make a dry granular herbicidal product, or further processed with surfactant. Alternatively, an aqueous slurry of glyphosate acid can be reacted with anhydrous ammonia or aqueous ammonia (ammonium hydroxide) to produce a concentrated solution or slurry of ammonium glyphosate. This solution or slurry then has to be dried if the desired finished product is a dry herbicidal composition.

Because anhydrous and aqueous ammonia are much lower-cost sources of the ammonium cation than ammonium bicarbonate, numerous efforts have been made to develop processes wherein glyphosate acid is reacted with anhydrous or aqueous ammonia, yet wherein a dry ammonium glyphosate composition is produced. U.S. Pat. No. 5,614,468 to Kramer et al. discloses such a process wherein solid particulate glyphosate acid is reacted with aqueous ammonia, and U.S. Pat. No. 5,633,397 to Gillespie et al. discloses such a process wherein solid particulate glyphosate acid is reacted with anhydrous ammonia gas.

Processes wherein the acid-base reaction takes place in an aqueous medium, generating a concentrated aqueous solution of ammonium glyphosate, are easier to control than the above solid-state processes. In addition, the exothermic nature of the reaction gives rise to a need for dissipation of heat, which presents much fewer problems in an aqueous medium because of the much greater ease of ensuring adequate mixing and thereby heat exchange than is possible in a solid-state process. There is therefore a long-felt need in the art to develop an efficient aqueous slurry process for making ammonium glyphosate wherein the end-product is a water-soluble dry particulate composition.

Dry particulate compositions of agricultural chemicals such as herbicides are typically powders or granules, for example water-soluble powders or granules. Granules are typically aggregates of smaller primary particles, while powders are typically formed of unaggregated primary particles. Water-soluble powders are not generally well favored because they tend to be dusty. Water-soluble granules are preferred over water-soluble powders, but have a much smaller surface area to volume ratio that tends to retard the process of dissolution, especially in cold water.

The present invention provides a process for making a dry particulate ammonium glyphosate composition that is less dusty than a powder but has a large surface area to volume ratio, promoting a rapid rate of dissolution, even in cold water. The composition takes the form of flakes.

SUMMARY OF THE INVENTION

Figure 1:
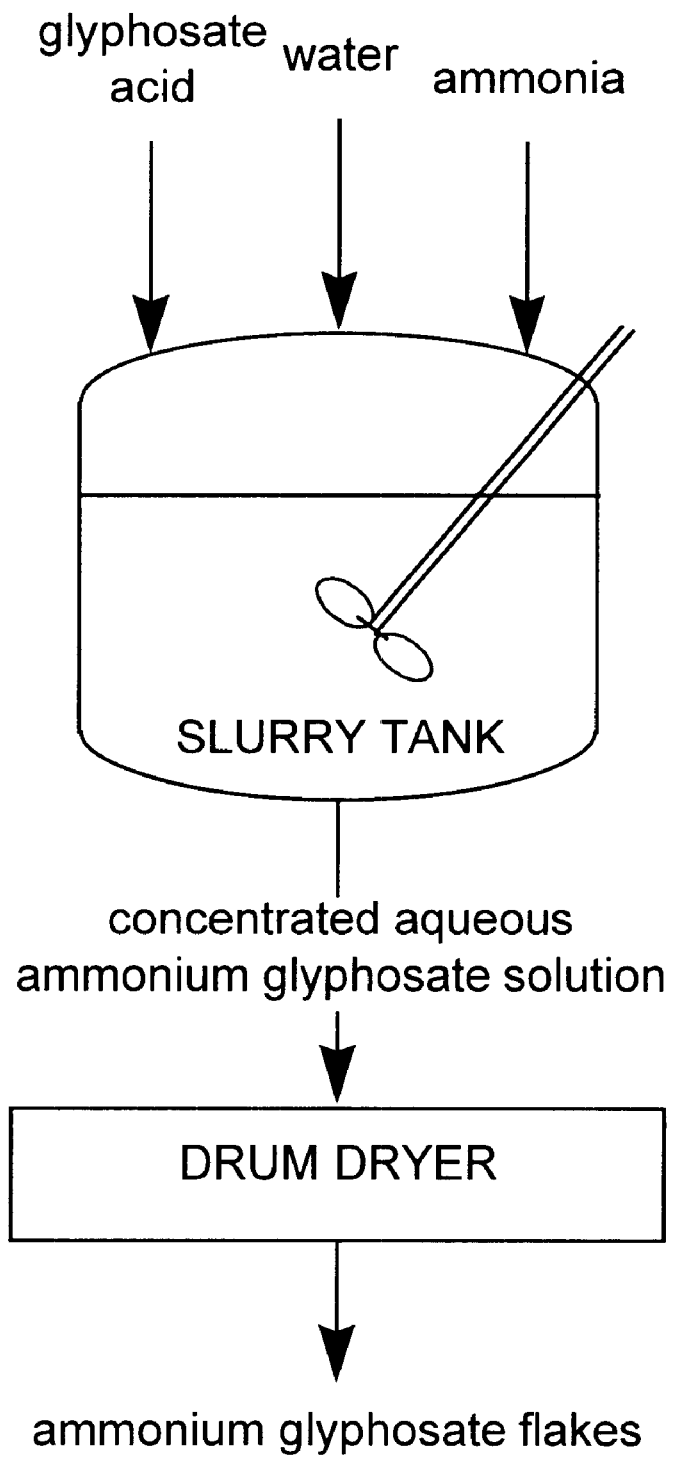
FIG. 1 shows a process flow diagram of a process of the invention.

There is now provided a process for preparing ammonium glyphosate flakes comprising (a) mixing (i) solid particulate glyphosate acid, (ii) water in an amount of about 0.5 to about 3 parts by weight per part by weight of glyphosate acid, and (iii) a base that supplies ammonium cations, in an amount of about 0.8 to about 1.25 mole equivalents of ammonia per mole of glyphosate acid, to form an aqueous reaction medium; (b) allowing the glyphosate acid to react with the base in the reaction medium to form a reaction product comprising a concentrated aqueous solution of ammonium glyphosate; (c) drying the reaction product by contact thereof with a heated surface to form, primarily by evaporation of water, a solid deposit on the heated surface; and (d) scraping the solid deposit off the heated surface to recover dry flakes of ammonium glyphosate.

Preferably the order of mixing in step (a) is to mix solid particulate glyphosate acid and water with agitation to form a slurry, and thereafter to add to the slurry, with continued agitation, the base that supplies ammonium cations.

Preferably steps (c) and (d) are accomplished by feeding the reaction product at a suitable rate on to the converging surfaces of two parallel counter-rotating internally heated cylinders having a gap between them of about 2 to about 10 mm to cause evaporation of water and form a solid deposit on the surfaces of the cylinders, and removing the solid deposit in the form of flakes by means of stationary scrapers against which the cylinders rotate.

DETAILED DESCRIPTION OF THE INVENTION

In the first step of a preferred process of the invention, i.e., step (a) as defined above, 1 part by weight of solid particulate glyphosate acid is added to about 0.5 to about 3 parts by weight of water and sufficient agitation is applied thereto to form a slurry. The glyphosate acid is preferably evenly dispersed in the slurry, but agglomeration of glyphosate acid particles into small aggregates is generally not detrimental. The relative amounts of water and glyphosate acid used to make the slurry are not narrowly critical within the range indicated above. However, it is generally desirable to produce, in step (b) that follows, an ammonium glyphosate solution of a high concentration, for example about 40% to about 60% by weight; this means that in step (a) for every 100 kg (on a dry basis) of glyphosate acid in the slurry it is desirable to have about 73 to about 165 kg of water.

Any grade of particulate glyphosate acid can be used. Technical grade glyphosate acid, for example in the form of wet cake having about 8% to about 12% moisture content, has been found to be suitable, but if desired the glyphosate acid can be pre-dried and/or pre-ground. Where an amount or concentration of glyphosate acid or of ammonium glyphosate is specified herein, it is to be understood to exclude moisture that may be present but to include minor amounts or concentrations of impurities. Typically technical grade glyphosate acid wet cake has a glyphosate assay, on a dry basis, of about 95% or higher, indicating that such impurities constitute less than about 5% by weight of technical grade glyphosate acid.

Other materials can optionally be added to or present in the slurry. For example, a small amount of sodium sulfite can be added to inhibit nitrosamine formation. Agitation is required to make and keep the slurry homogeneous; this can be supplied by any suitable means.

Illustratively, a slurry can be made by placing 75 kg water in a tank, and adding, with agitation, 100 kg glyphosate wet cake at 10% moisture content and, if desired, 0.4 kg sodium sulfite.

In the same preferred process of the invention, a base that supplies ammonium cations is then fed into the slurry tank containing the glyphosate acid so as to cause, in step (b), an acid-base reaction forming ammonium glyphosate. Any base that supplies ammonium cations can be used, including ammonium carbonate and ammonium bicarbonate. However, it is generally preferred to use aqueous or anhydrous ammonia. If aqueous ammonia (i.e., ammonium hydroxide) is used, the amount of water supplied by the aqueous ammonia further dilutes the slurry. Typically aqueous ammonia contains about 29% by weight ammonia and can therefore be considered to supply about 71% of its weight as water. This should be factored into the calculation of the amount of water to be used in making the glyphosate acid slurry. Anhydrous ammonia can be supplied in the liquid or gaseous state.

Although the mixing and reaction steps (a) and (b) respectively are described herein for convenience and clarity as separate steps, it will be recognized by those of skill in the art that the acid-base reaction commences as soon as the first portion of acid and base come together in the aqueous reaction medium. Indeed, the reaction can already be substantially completed by the time addition of the base to the slurry is completed.

Preferably aqueous or anhydrous ammonia is added in an approximately stoichiometric amount to result in the formation of monoammonium glyphosate. If less than 1 mole equivalent of ammonia is added per mole of glyphosate acid, a fraction of the glyphosate acid will remain unneutralized. If this fraction is small, for example less than about 20%, resulting in the presence of at least about 4 moles of ammonium glyphosate per mole of unneutralized glyphosate acid, it is generally not unacceptable.

On the other hand, if more than 1 mole equivalent of ammonia is added per mole of glyphosate acid, a fraction of the glyphosate can be considered to be present in the form of the diammonium salt. Subsequent drying of the reaction product will, in such a situation, tend to lead to volatilization of ammonia. For this reason the amount of ammonia added in step (a) should be kept below about 1.25 mole equivalents per mole of glyphosate acid. However, it is preferred that about 0.95 to about 1.05 mole equivalents of ammonia are added per mole of glyphosate acid.

The reaction of ammonia with glyphosate acid is exothermic. Continued agitation of the slurry in step (b) is important to provide efficient heat transfer as well as to ensure a complete and uniform reaction. With conversion of glyphosate acid to ammonium glyphosate, the glyphosate becomes solubilized in the water. The product of the reaction step therefore comprises a concentrated aqueous solution of ammonium glyphosate. A "concentrated" aqueous solution of ammonium glyphosate herein means a solution containing at least about 20%, preferably at least about 40%, and more preferably at least about 55%, by weight of ammonium glyphosate. The upper limit is the limit of solubility of ammonium glyphosate in water, which is temperature dependent.

While the reaction product comprises such a concentrated aqueous solution, it can also contain undissolved solid particles, in which case the reaction product is more accurately described as a slurry. Such undissolved solid particles can be of ammonium glyphosate or of unneutralized glyphosate acid.

It is preferred to maintain the reaction product at an elevated temperature, for example about 65° C. to about 85° C., for maximum solubility of the ammonium glyphosate.

The next step of the process, i.e., step (c) as defined above, comprises drying this reaction product by contact thereof with a heated surface to form, primarily by evaporation of water, a solid deposit on the heated surface. Drying methods other than those involving contact with a heated surface, for example flash drying and spray drying methods and modifications thereof, have been found to produce unsatisfactory results in terms of process efficiency.

The heated surface is preferably the surface of a cylinder such as a drum or roller, and is preferably a metallic surface providing good heat conductivity while being not subject to corrosion in contact with the reaction product of step (b). Suitable metallic surfaces are provided, for example, by stainless steel or chromium plate. In the case of a cylinder, heat is preferably provided to the surface from a heat source or vector in the interior of the cylinder. Superheated steam has been found to be a suitable heat vector. The temperature of the heated surface can be controlled by adjusting the pressure under which the superheated steam is supplied to the cylinder; pressures from about 250 to about 1000 kPa can illustratively be applied, but preferably the steam pressure is about 500 to about 900 kPa. Higher steam pressures within these ranges, generating higher surface temperatures, tend to lead to faster and more complete drying. Temperatures should not be so high, nor residence time of the solid deposit on the heated surface so long, that the glyphosate undergoes thermal decomposition, a process that occurs at 200–230° C. as described by J. E. Franz el al. in American Chemical Society Monograph 189, *Glyphosate, a Unique Global Herbicide,* 1997, pp. 27 and 244. Some volatilization of ammonia can be expected during the drying step, but provided temperature of the heated surface is not excessive and residence time is not too long, such volatilization is generally minimal and presents no problems.

The effect of drying is to form a solid deposit on the heated surface. In step (d) this solid deposit is recovered in the form of flakes, by scraping the deposit off the surface. When the drying step is performed efficiently the moisture content of the flakes is typically below about 3% by weight and is preferably below about 1.5%, more preferably below about 1%, by weight. Further drying of the flakes, for example in an oven and/or under vacuum, can be carried out if desired.

It will be clear to those of skill in the art from the above description that the type of apparatus known as a drum dryer or roller dryer can provide the requisite heated surface for step (c) of the present process. It will also be clear that other types of apparatus having a heated surface can likewise be suitable. The following description of the use of a drum or roller dryer apparatus in performing step (c) of the process is not to be construed as limiting the invention to use of such apparatus for performing this process step. Drum or roller dryers are described, for example, in *Encyclopedia of Chemical Processing and Design,* Ed. J. J. McKetta, Vol. 17, Pub. Marcel Dekker, Inc., 1983, pp. 17–19; in *Ullmann's Encyclopedia of Industrial Chemistry,* 5th Edition, Vol. B2, Pub. VCH, 1988, pp. 4.25–4.27; and in *Kirk-Othmer Encyclopedia of Chemical Technology,* 4th Edition, Vol. 8, Pub. John Wiley & Sons, 1993, pp. 512–514. Other designs of contact dryers that can be substituted if desired are described in these publications.

Drum dryers can have a single rotating heated drum or, more suitably for the present process, two parallel heated drums that rotate in contrary senses, one clockwise and the other counterclockwise. The axis of rotation is normally horizontal or very nearly horizontal. In operation the surfaces of the parallel drums are separated from each other by a very narrow, generally adjustable, gap known as the "nip". The width of the gap, known as "drum clearance", at the nip is typically set at about 2 to about 10 mm, preferably about 3 to about 7 mm. Preferably the drums rotate in such a way that the surfaces converge above the nip, thereby feeding any material deposited on either or both surfaces into the nip.

In performing step (c) of the present process in such a drum dryer, the reaction product of step (b) is fed on to the converging surfaces of the parallel drums. Feeding of the reaction product can be by spraying, but greater efficiency is generally obtained by permitting the reaction product to flow from a pipe, the tip of which swings like a pendulum over the converging surfaces of the drums and over the nip. Rotational speed of the drums and temperature of the surfaces are controlled so as to permit evaporation of most of the water in the reaction product above the nip. Further drying takes place in and below the nip, resulting in a thin, more or less continuous, solid deposit that adheres to the surfaces of both drums. It has been found that the process operates most efficiently when drying above the nip is such as to result in accumulation of a thick mash in the nip.

In a typical drum dryer, a stationary scraper blade is disposed parallel to the axis of each drum, a scraping edge of the blade contacting the surface of the drum. The blade is angled so that the scraping edge is oriented against the rotational movement of the drum surface. As the drum surface moves against the scraping edge of the blade, any solid deposit thereon is removed from the surface and falls or is transported to a hopper or other collecting vessel. During scraping the solid material breaks into small flakes.

Precise location of the scraper blades relative to the nip of the drums is not critical, but it is generally desired for maximum drying to permit a fairly long period of contact of the solid deposit with the heated surfaces of the drums, and for this reason a suitable placement for the scaper blade for each drum is approximately diametrically opposite the nip, i.e., about 180° from the nip in the sense of rotation of the drum, or slightly above that location. A typical placement is about 180° to about 220°, for example about 200°, from the nip.

Ammonium glyphosate flakes prepared by the process provided herein have a number of advantages over dry ammonium glyphosate compositions previously described. The flakes break readily to form smaller flakes but are relatively non-dusty. The flakes dissolve rapidly and completely in water to form a solution suitable for application to plants as a herbicide. Usefully and illustratively about 1 to about 100 g, more typically about 2 to about 20 g, of ammonium glyphosate flakes are dissolved in 1 liter of water to make an application solution. Surfactant and/or other ingredients can if desired also be added to the application solution.

The product of the present process is especially suited to packaging in small packages such as plastic or foil sachets or water-soluble bags, illustratively containing about 10 to about 1000 g of flakes. However, the invention is not limited by such packaging. If desired, any conventional packaging system, including boxes or drums, of any size can be used. The product can alternatively be shipped in bulk form.

The product can also be used as an intermediate for further processing. For example, the flakes can be milled to form a powder. Such powder, or the flakes themselves, can form a raw material for a granulation process, optionally involving addition of surfactant.

EXAMPLES

The following Examples are provided for illustrative purposes only and are not intended to limit the scope of the present invention. The Examples will permit better understanding of the invention and perception of its advantages and certain variations of execution.

In a program of evaluation of drying methods for a concentrated ammonium glyphosate solution such as is produced by reacting glyphosate acid with aqueous or anhydrous ammonia in a slurry, the following systems and apparatus were tested.

Example 1

This Example of a comparative process comprises flash drying in a Pulvocron™ PC-20 air classifying mill (Hosokawa Bepex Corp., Minneapolis, Minn.).

To simulate the reaction product of a glyphosate acid slurry with ammonia, a 56% by weight ammonium glyphosate solution was prepared by dissolving dry ammonium glyphosate, technical grade (MON 8750 of Monsanto) in water. To ensure dispersion of undissolved solids, drums containing the ammonium glyphosate solution were agitated on a drum roller for about 90 minutes prior to the flash drying tests.

The liquid ammonium glyphosate solution was fed to a Pulvocron™ PC-20 by a Moyno pump at feed rates ranging from 63.5 to 204 kg/h in individual tests. In the Pulvocron the liquid was met by air heated to a temperature ranging from 89° C. to 268° C. at an air flow rate ranging from 23 to 36 m³/minute in individual tests. Beater plates in the Pulvocron threw the liquid against a segmented liner while the hot air flashed off the water. Various combinations of beater plates were installed in individual tests.

In all tests, build-up of dried solid material occurred on the walls and beater plates of the Pulvocron, eventually plugging the system and preventing discharge of dry product. No improvement was noted even with removal of the air classifier from the Pulvocron in an effort to improve discharge. Back-mixing of already dried material with the liquid feed also did not help.

Example 2

This Example of a comparative process comprises drying in a Unison™ spray dryer (Hosokawa Bepex Corp., Minneapolis, Minn.).

In prior tests with conventional spray dryers fitted with centrifugal atomizers, the liquid was sprayed towards the walls of the spray drying chamber, where dried material accumulated. None of the dried material was discharged. By contrast, the Unison™ spray dryer uses a pulsed combustion system to provide a sonic wave that atomizes a liquid feed. This atomization results in a more gentle release of the liquid feed into the chamber, with less tendency for contact with and therefore adhesion of dried material to the walls.

The dryer tested had a spray drying chamber having an upper cylindrical section of diameter 1.8 m and height 4.3 m, and a lower 70° conical section of height 2.1 m. Heated air and liquid feed were introduced at the top of the chamber and air and dried product discharged through a 300 mm diameter duct at the bottom. Dried product was fed to a cyclone separator and baghouse for collection.

As feed liquids for testing this system, ammonium glyphosate solutions were prepared by dissolving MON 8750 in water as for the flash drying test above. A 50% by weight ammonium glyphosate solution was prepared for one test, while for other tests aqueous slurries were used containing ammonium glyphosate above its limit of solubility. These slurries contained 60% or 70% total "solids", i.e., including dissolved ammonium glyphosate.

The liquid feed was preheated to 32° C., 66° C. and 74° C. in individual tests. Air temperature was about 255° C. Feed rate was set to 182 kg/h. It was found that the 70% ammonium glyphosate slurry was too viscous to feed efficiently, while the 50% ammonium glyphosate solution, when used as the feed, resulted in rapid build-up of a hard-to-remove glassy material on the chamber walls. It is believed that absence of solid particles in the feed inhibited rapid crystallization of the ammonium glyphosate, resulting in the glassy deposit.

By contrast, the 60% ammonium glyphosate slurry, preheated to 32° C. or 66° C., gave effective spray drying. Yields were 90% and 77% respectively. Some build-up of white powdery material was observed on the walls, particularly in the lower conical section near the discharge outlet, but this was insufficient to adversely affect the spray drying operation. Moisture content of the powdery product ranged from 1.4% to 1.7% by weight.

In a repeat test using 60% slurry at 66° C., the discharge outlet became plugged with loose and friable material and the system shut down after 40 minutes.

Example 3

This Example of a comparative process comprises drying in a spray dryer (APV Anhydro, Copenhagen, Denmark).

The spray dryer tested at APV had a centrifugal atomizer and a built-in air broom to cool and sweep the walls and bottom of the spray drying chamber. The chamber was cylindrical, 3.0 m in diameter and 3.0 m high, with a flat bottom. Liquid feed and air were introduced at the top and dried product discharged at the bottom. Product was fed to a cyclone separator and baghouse for collection.

The liquid feed for all tests of the APV spray dryer was a 60% ammonium glyphosate slurry, prepared exactly as for Example 2 above.

Regardless of feed rate, air temperature and air flow to the air broom, product dried in the APV spray dryer failed to discharge. It was concluded that this apparatus was not suitable for drying ammonium glyphosate.

Example 4

This Example of a comparative process comprises drying in a fluidized bed spray dryer (APV Anhydro, Copenhagen, Denmark).

The dryer used for these tests had a spray drying chamber having an upper cylindrical section of diameter 1.5 m and height 1.5 m and a lower conical section of height 0.9 m, discharging to a fluidized bed immediately below. Discharge from the fluidized bed was from the bottom via a rotary air lock. Material was fed from the fluidized bed to a cyclone separator, from which fine particles were recycled to the conical section of the drying chamber.

The same 60% ammonium glyphosate slurry was used as in previous Examples. Air inlet temperature in the spray drying chamber was 215° C. and in the fluidized bed 100° C. About 30 kg ammonium glyphosate powder was added to the fluidized bed to prime the system.

Dried product failed to discharge from the spray drying chamber to the fluidized bed because of accumulation and bridging in the conical section of the chamber. It is believed that design modifications could alleviate this problem; however, from all tests conducted it was concluded that spray drying was not the most appropriate method of converting an ammonium glyphosate solution or slurry to dry powder on a manufacturing scale.

Example 5

This Example illustrative of the invention comprises contact drying with a 6 inch×6 inch (150 mm×150 mm) Buflovak™ atmospheric double drum dryer (Blaw Knox Corp., Buffalo, N.Y.).

Before attempting to dry ammonium glyphosate in a 24 inch×24 inch (600 mm×600 mm) Buflovak™ atmospheric double drum dryer, a feasibility study was conducted using a 6 inch×6 inch (150 mm×150 mm) laboratory model. The dimensions (e.g., 6 inch×6 inch) relate to the diameter and length of each drum. The 6 inch×6 inch laboratory model has a total drum surface area of about 1.57 square feet (0.145 m$^2$), which represents about 6.3% of the surface area of a 24 inch×24 inch model, i.e., about 25 square feet (2.31 m$^2$).

For the feasibility study, a 49% by weight ammonium glyphosate solution was prepared by dissolving MON 8750 in water. When fed to the drum dryer at a temperature of 50° C., the solution was successfully dried to flakes having a moisture content of 1.2%. A production rate of 10.6 kg/m$^2$/h was calculated.

Example 6

This Example illustrative of the invention comprises contact drying with a 24 inch×24 inch (600 mm×600 mm) Buflovak™ atmospheric double drum dryer (Blaw Knox Corp., Buffalo, N.Y.).

For this series of tests, a 59–60% by weight ammonium glyphosate slurry was prepared by dissolving MON 8750 in water. About 2–5% of the ammonium glyphosate remained undissolved. The slurry was fed to a 24 inch×24 inch double drum dryer at a temperature of 74° C., using a pendulum feed system. Both drums were internally heated using superheated steam, initially at a pressure of 95 psig (656 kPa), and were rotated initially at 3 rpm. In a run of about 10–15 minutes, flakes of dry ammonium glyphosate of good appearance were produced having a moisture content of 1.1 %, at a production rate of 28.5 kg/m$^2$/h.

Data for this and other runs, each of about 10–15 minutes, where various parameters were varied, are shown in the table below.

| run no. | 1 | 2 | 3 | 4 | 5 |
|---|---|---|---|---|---|
| % ammonium glyphosate in feed | 59 | 59 | 59 | 60 | 51[1] |
| feed temperature, ° C. | 74 | 69 | 64 | 88[2] | 56 |
| steam pressure, kPa | 656 | 676 | 676 | 869 | 856 |
| rotation speed of drums, rpm | 3.0 | 4.5 | 6.0 | 5.0 | 3.5 |
| drum clearance at nip, mm | 4.6 | 4.3 | 4.3 | 4.4 | 4.6 |
| production rate, kg/m$^2$/h | 28.5 | 43.6 | 35.4 | 42.4 | 30.1 |
| % moisture content of product | 1.1 | 0.6 | 0.9 | 0.7[3] | 0.7 |

[1] at this reduced ammonium glyphosate concentration, feed was a clear solution
[2] at this increased temperature, feed was a clear solution
[3] mean of three samples ranging from 0.5% to 0.9% moisture content Optimum conditions in this test series appeared to be with a 59–60% ammonium glyphosate slurry and a drum rotation speed of about 4.5 to 5 rpm. A longer production run, lasting about 60 minutes, was therefore made using a 60% slurry at a feed temperature of 66° C., 662 kPa steam pressure and 4.5 rpm rotation speed. Drum clearance at the nip was narrowed slightly to 3.0 mm. This run was very successful, giving a product having an average moisture content of about 0.8% at a production rate of 39.5 kg/m$^2$/h.

Example 7

This Example of a process of the invention comprises contact drying with a 24 inch×24 inch (600 mm×600 mm) Buflovak™ atmospheric double drum dryer (Blaw Knox Corp., Buffalo, N.Y.).

Ammonium glyphosate feed for this series of tests was made by preparing an aqueous slurry of glyphosate wet cake and neutralizing stoichiometrically with aqueous ammonia to produce a 58% by weight solution or slurry of ammonium glyphosate. For some tests this feed was slightly diluted with water.

Test runs were made using the 24 inch×24 inch drum dryer as in Example 6. Data are shown in the table below.

| run no. | 1 | 2 | 3 | 4 | 5 | 6 | 7 | 8 |
|---|---|---|---|---|---|---|---|---|
| duration of run, minutes | 15 | 60 | 292 | 15 | 60 | 60 | 175 | 53 |
| % ammonium glyphosate in feed | 58 | 58 | 58 | 54 | 54 | 54 | 56 | 56 |
| feed temperature, ° C. | 96 | 96 | 84 | 63 | 63 | 63 | 82 | 83 |
| steam pressure, kPa | 662 | 718 | 745 | 759 | 704 | 718 | 828 | 828 |
| rotation speed of drums, rpm | 4.3 | 4.5 | 4.5 | 4.3 | 4.3 | 4.0 | 4.0 | 3.0 |
| drum clearance at nip, mm | 3.3 | 4.3 | 4.0 | 3.3 | 3.0 | 3.0 | 3.0 | 7.3 |
| production rate, kg/m$^2$/h | 34.0 | 38.6 | 38.8 | 32.6 | 31.9 | 30.5 | 35.4 | 43.2 |
| % moisture | 1.8 | 1.2 | 1.4 | 1.6 | 1.4 | 1.4 | 0.9 | 2.0 |

-continued

| run no. | 1 | 2 | 3 | 4 | 5 | 6 | 7 | 8 |
|---|---|---|---|---|---|---|---|---|
| content of product | | | | | | | | |

Example 8

This Example of a process of the invention comprises contact drying with a 24 inch×24 inch (600 mm×600 mm) Buflovak™ atmospheric double drum dryer (Blaw Knox Corp., Buffalo, N.Y.).

Ammonium glyphosate feed for this series of tests was made as for Example 7 but at lower concentration and at three levels of neutralization: stoichiometric (i.e., 100% neutralization with ammonia), 102% and 104%.

Test runs were made using the 24 inch×24 inch drum dryer as in Examples 6 and 7. Data are shown in the tables below (n.r.=not recorded).

| run no. | 1 | 2 | 3 | 4 | 5 | 6 | 7 |
|---|---|---|---|---|---|---|---|
| duration of run, minutes | 30 | 20 | 15 | 15 | 15 | 15 | 20 |
| % ammonium glyphosate in feed | 45 | 45 | 45 | 45 | 45 | 45 | 45 |
| degree of neutralization, % | 100 | 100 | 100 | 102 | 102 | 102 | 102 |
| feed temperature, °C. | 82 | 83 | 82 | 97 | n.r. | 84 | 81 |
| steam pressure, kPa | 518 | 690 | 814 | 414 | 518 | 690 | 828 |
| rotation speed of drums, rpm | 5.0 | 5.0 | 5.0 | 5.0 | 5.0 | 5.0 | 5.0 |
| drum clearance at nip, mm | 2.7 | 5.2 | 6.7 | 3.0 | 3.0 | 3.3 | 3.6 |
| production rate, kg/m²/h | 31.6 | 47.7 | 52.1 | 23.6 | 37.7 | 38.5 | 42.0 |
| % moisture content of product | 2.1 | 1.8 | 1.3 | 3.4 | 2.0 | 1.2 | 1.0 |

| run no. | 8 | 9 | 10 | 11 | 12 | 13 | 14 | 15 |
|---|---|---|---|---|---|---|---|---|
| duration of run, minutes | 10 | 10 | 10 | 10 | 10 | 20 | 70 | 78 |
| % ammonium glyphosate in feed | 45 | 45 | 45 | 45 | 45 | 45 | 45 | 45 |
| degree of neutralization, % | 104 | 104 | 104 | 104 | 104 | 104 | 104 | 102 |
| feed temperature, °C. | 80 | 89 | 88 | 86 | 86 | 80 | 83 | 82 |
| steam pressure, kPa | 414 | 414 | 518 | 690 | 807 | 821 | 690 | 690 |
| rotation speed of drums, rpm | 3.0 | 5.0 | 5.0 | 5.0 | 5.0 | 3.0 | 5.0 | 5.0 |
| drum clearance at nip, mm | 3.3 | 3.3 | 3.6 | 3.3 | 5.2 | 5.5 | 3.3 | 3.3 |
| production rate, kg/m²/h | 19.5 | 26.5 | 34.2 | 33.6 | 30.1 | 35.7 | 34.0 | 37.8 |
| % moisture content of product | 2.0 | 2.3 | 1.4 | 0.9 | 0.9 | 0.5 | 1.4 | 1.1 |

Example 9

This Example of a process of the invention comprises contact drying with a 24 inch×24 inch (600 mm×600 mm) Buflovak™ atmospheric double drum dryer (Blaw Knox Corp., Buffalo, N.Y.).

Ammonium glyphosate feed for this series of tests was made by preparing an aqueous slurry of glyphosate wet cake and neutralizing stoichiometrically with aqueous ammonia to produce solutions or slurries of ammonium glyphosate at various concentrations.

Test runs were made using the 24 inch×24 inch drum dryer as in Examples 6–8. Data are shown in the table below (n.r.=not recorded).

| run no. | 1 | 2 | 3 | 4 | 5 | 6 |
|---|---|---|---|---|---|---|
| duration of run, minutes | 104 | 99 | 140 | 134 | 140 | 129 |
| % ammonium glyphosate in feed | 53 | n.r. | 47 | 59–64 | 57 | 59 |
| feed temperature, °C. | 77 | 82 | 74 | 81 | 79 | 79 |
| steam pressure, kPa | 814 | 821 | 814 | 828 | 828 | 828 |
| rotation speed of drums, rpm | 4.0 | 5.0 | 4.0 | 4.0 | 4.0 | 4.0 |
| drum clearance at nip, mm | 4.9 | 5.5 | 5.5 | 5.5 | 4.6–7.0 | 5.5 |
| production rate, kg/m²/h | 47.7 | 54.8 | 45.4 | 45.7 | 46.2 | 52.1 |
| % moisture content of product | 1.6 | 1.3 | 1.5 | 1.2 | 1.6 | 1.2 |

From the tests described in Examples 5–9 herein, it is clear that drum drying is an acceptable drying method for a concentrated ammonium glyphosate solution prepared by reacting glyphosate acid and ammonia in an aqueous slurry. Further optimization of the drum drying process can readily be performed by one of skill in the art by routine testing.

The preceding description of specific embodiments of the present invention is not intended to be a complete list of every possible embodiment of the invention. Persons skilled in this field will recognize that modifications can be made to the specific embodiments described here that remain within the scope of the present invention.

What is claimed is:

1. A process for preparing ammonium glyphosate flakes, comprising
    (a) mixing (i) solid particulate glyphosate acid, (ii) water in an amount of about 0.5 to about 3 parts by weight per part by weight of glyphosate acid, and (iii) a base that supplies ammonium cations, in an amount of about 0.8 to about 1.25 mole equivalents of ammonia per mole of glyphosate acid, to form an aqueous reaction medium;
    (b) allowing the base to react with the glyphosate acid in the aqueous reaction medium to form a reaction product comprising a concentrated aqueous solution of ammonium glyphosate;
    (c) drying the reaction product by contact thereof with a heated surface to form, primarily by evaporation of water, a solid deposit on the heated surface; and
    (d) scraping the solid deposit off the heated surface to recover dry flakes of ammonium glyphosate.

2. The process of claim 1 wherein the order of mixing in step (a) is to mix the glyphosate acid and the water with agitation to form a slurry and thereafter to add to the slurry, with continued agitation, the base that supplies ammonium cations.

3. The process of claim 1 wherein the base that supplies ammonium cations is anhydrous or aqueous ammonia.

4. The process of claim 1 wherein the drying step is performed by feeding the reaction product at a suitable rate on to the converging surfaces of two parallel counter-rotating internally heated cylinders having a gap between them of about 2 to about 10 mm to cause evaporation of water and form a solid deposit on the surfaces of the cylinders, and wherein the scraping step is performed by removing the solid deposit in the form of flakes by means of stationary scrapers against which the cylinders rotate.

5. The process of claim 4 wherein the drying and scraping steps are performed with a drum dryer.

* * * * *